(12) United States Patent
Reel et al.

(10) Patent No.: US 7,177,023 B2
(45) Date of Patent: Feb. 13, 2007

(54) FLUORESCENT LIGHT DETECTION

(75) Inventors: Richard T. Reel, Hayward, CA (US); Eric S. Nordman, Palo Alto, CA (US)

(73) Assignee: Applera Corporation, Foster City, CA (US)

( * ) Notice: Subject to any disclaimer, the term of this patent is extended or adjusted under 35 U.S.C. 154(b) by 371 days.

(21) Appl. No.: 10/805,096

(22) Filed: Mar. 19, 2004

(65) Prior Publication Data

US 2005/0206900 A1    Sep. 22, 2005

(51) Int. Cl.
*G01J 3/30* (2006.01)
(52) U.S. Cl. .................................. 356/317
(58) Field of Classification Search ............. 356/311, 356/317, 318, 344; 250/458.1, 459.1, 461.2; 422/82.07, 82.08; 436/172
See application file for complete search history.

(56) References Cited

U.S. PATENT DOCUMENTS

| | | | |
|---|---|---|---|
| 4,714,345 A | 12/1987 | Schrader | |
| 5,021,646 A | 6/1991 | Weinberger et al. | |
| 5,192,980 A * | 3/1993 | Dixon et al. | 250/458.1 |
| 5,239,360 A | 8/1993 | Moring et al. | |
| 5,274,240 A * | 12/1993 | Mathies et al. | 250/458.1 |
| 5,372,783 A | 12/1994 | Lackie | |
| 5,430,541 A | 7/1995 | Sapp et al. | |
| 5,434,664 A | 7/1995 | Sapp | |
| 5,484,571 A * | 1/1996 | Pentoney et al. | 422/82.08 |
| 5,644,396 A * | 7/1997 | Hopkins, II | 356/301 |
| 5,926,271 A | 7/1999 | Couderc et al. | |
| 6,017,434 A | 1/2000 | Simpson et al. | |
| 6,184,990 B1 | 2/2001 | Amirkhanian et al. | |
| 6,239,871 B1 | 5/2001 | Gilby | |
| 6,636,304 B2 | 10/2003 | Gilby | |
| 6,686,582 B1 * | 2/2004 | Volcker et al. | 250/216 |
| 6,690,647 B1 | 2/2004 | Tang et al. | |
| 6,814,933 B2 * | 11/2004 | Vuong | 422/82.05 |
| 2001/0041843 A1 * | 11/2001 | Modell et al. | 600/473 |
| 2002/0030810 A1 | 3/2002 | Gilby | |
| 2003/0048539 A1 | 3/2003 | Oostman et al. | |
| 2003/0222223 A1 | 12/2003 | Kamei et al. | |

OTHER PUBLICATIONS

Sweedler, J.V. et al. "Fluorescence Detection in Capillary Zone Electrophoresis Using a Charge-Coupled Device with Time-Delayed Integration." Analytical Chemistry 1991, vol. 63, p. 496 (abstract only).*

International Search Report for Int'l Application No. PCT/US2005/009232 date mailed Sep. 1, 2005; along with Written Opinion of the ISA.

* cited by examiner

*Primary Examiner*—Gregory J. Toatley, Jr.
*Assistant Examiner*—Michael A. Lyons

(57) ABSTRACT

System and method for fluorescent light detection from biological samples to enhance the numerical aperture and/or reduce the cross-talk of the fluorescent light.

26 Claims, 18 Drawing Sheets

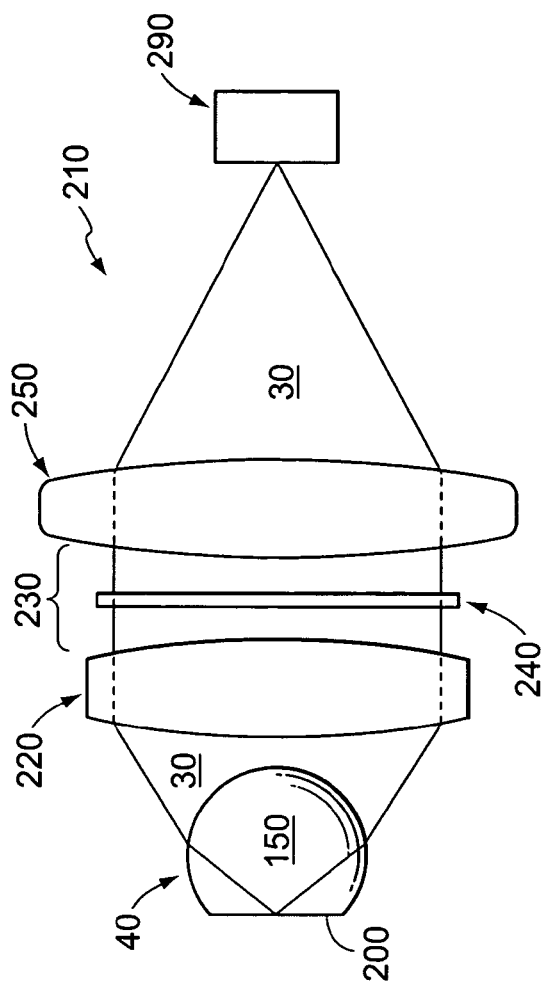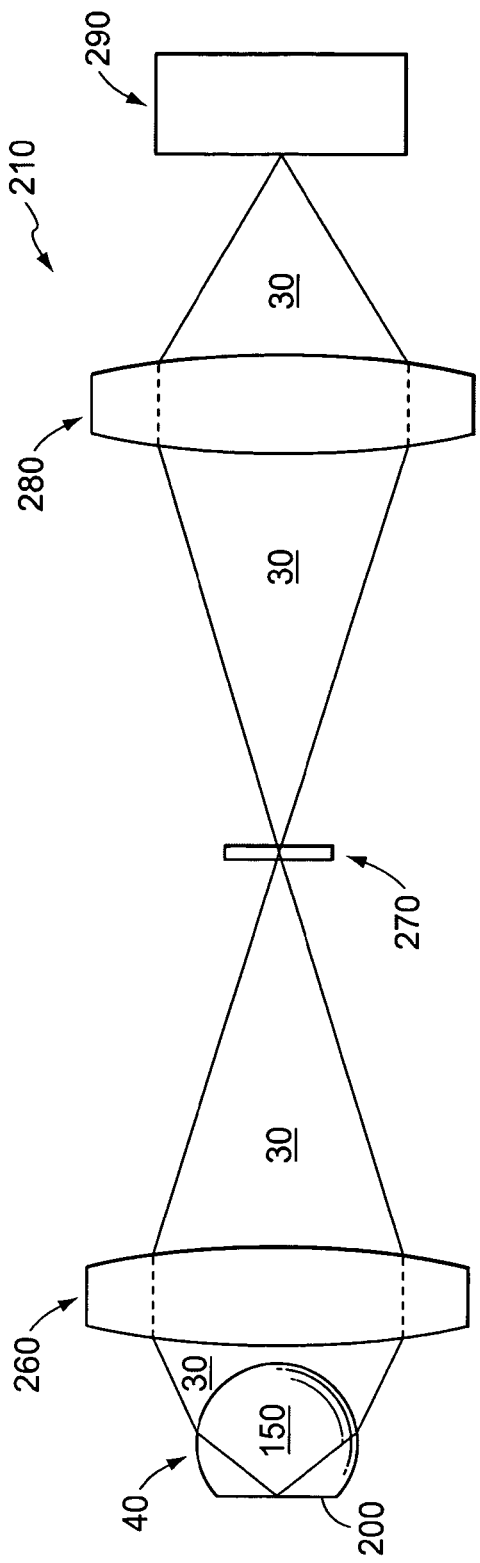

FLUORESCENT LIGHT DETECTION

FIELD

The present teachings relate to devices and methods for fluorescent light detection.

INTRODUCTION

Molecular biology and other sciences can utilize fluorescent detection because of its wide acceptance and sensitivity. Fluorescent light can be generated by exciting dyes in a sample using excitation light or chemical means. The fluorescent light emitted can be diffuse due to low concentrations of dye in the sample. It is desirable to collect more of the diffuse light to increase the efficiency of fluorescent detection.

Fluorescent light detection systems can benefit from corrective aberration. It is desirable to enhance the numerical aperture by changing the material of construction of a numerical aperture ("NA") enhancing optical element in the fluorescent light detection system such that the NA enhancing optical element is constructed of different material than the housing containing the sample. This can introduce spherical aberration into the system. It is desirable to eliminate the spherical aberration by positioning the housing in a source plane that is offset from the theoretical aplanatic source plane.

Increasing efficiency by collecting more light from fluorescent light detection systems can generate cross-talk between different samples. It is desirable to decrease the cross-talk by separating the light collected from different samples.

SUMMARY

According to various embodiments, the present teachings include a fluorescent light detection system for analyzing samples including a NA enhancing optical element comprising a truncated sphere, a plurality of housings for the samples, and a mask including at least one aperture adapted to reduce cross-talk of fluorescent light from the samples.

According to various embodiments, the present teachings include a fluorescent light detection system for analyzing samples including a NA enhancing optical element, a plurality of housings for the samples, a movable mask comprising at least one aperture adapted to reduce cross-talk of fluorescent light from the samples, and a translation mechanism for moving the mask.

According to various embodiments, the present teachings include a fluorescent light detection system for analyzing samples including a NA enhancing optical element, a plurality of housings for the samples, a mask comprising at least one aperture adapted to reduce cross-talk of fluorescent light from the samples, wherein the mask is positioned between the NA enhancing optical element the plurality of housings, and a translation mechanism for moving the plurality of housings.

According to various embodiments, the present teachings include a fluorescent light detection method for analyzing samples including providing a plurality of housings for the samples, providing a NA enhancing optical element, providing a mask, and positioning the mask to reduce cross-talk between fluorescent light from the samples.

According to various embodiments, the present teachings include a fluorescent light detection system for analyzing samples including a NA enhancing optical element including a truncated sphere and an offset, wherein a source plane of the truncated sphere and a back end of the truncated sphere bound the offset.

According to various embodiments, the present teachings include a fluorescent light detection system for analyzing samples including means for collecting light, means for housing the samples, and means for reducing cross-talk of fluorescent light from the samples.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate various embodiments. In the drawings.

FIGS. 6A–6B, 7–10 illustrate diagrammatical views of various embodiments of fluorescent light detection systems;

DESCRIPTION OF VARIOUS EMBODIMENTS

Figure 1:
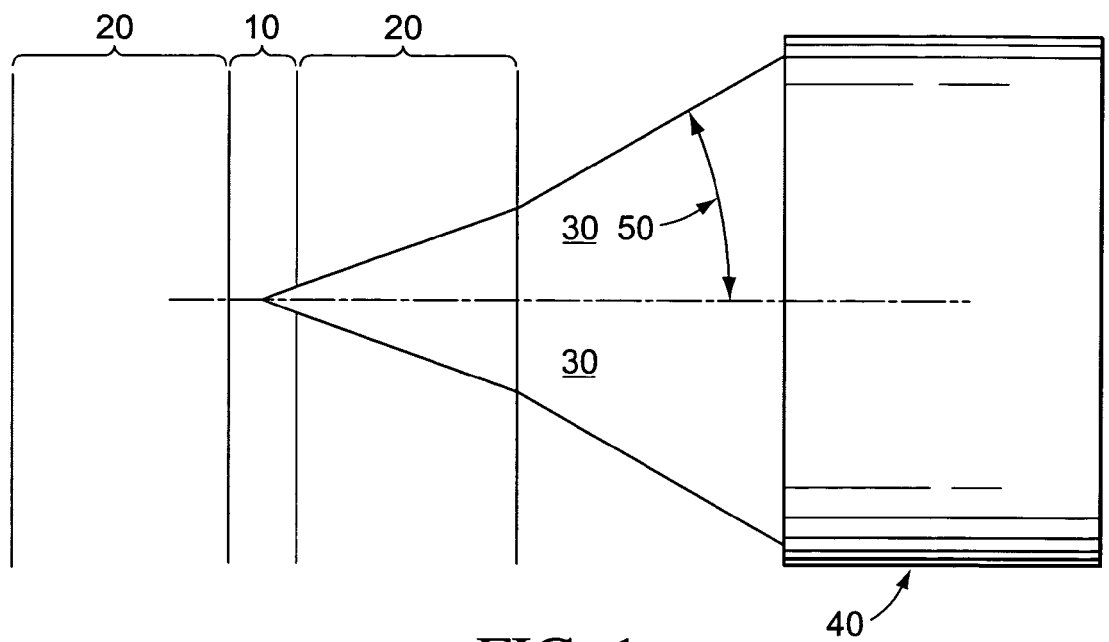
FIG. 1 illustrates a diagrammatical view of various embodiments of a sample, housing, and NA enhancing optical element.

Reference will now be made to various exemplary embodiments, examples of which are illustrated in the accompanying drawings. Wherever possible, the same reference numbers are used in the drawings and the description to refer to the same or like parts.

The term "cross-talk" as used herein refers to fluorescent light emitted from one sample appearing in the detection position of another sample. The samples can be in different housings or in the same housings. The cross-talk can be the result of reflection, scattering, and/or refraction from components in the system.

The term "light source" as used herein refers to a source of irradiance (can be measured in photons/mm$^2$) that can provide excitation that results in fluorescent emission. Irradiance can be related to fluorescent light because fluorescent light is proportional to the number of photons available from the light source for excitation. Light sources can include, but are not limited to, lasers, solid state laser, laser diode, diode solid state lasers (DSSL), vertical-cavity surface-emitting lasers (VCSEL), LEDs, phosphor coated LEDs, organic LEDs, inorganic-organic LEDs, LEDs using quantum dot technology, LED arrays, filament lamps, arc lamps, gas lamps, and fluorescent tubes. Light sources can have high irradiance, such as lasers, or low irradiance, such as LEDs.

The term "fluorescent light" as used herein refers to a light emitted by an excited sample. Fluorescent light can be emitted in all directions. Fluorescent light can be related to detection signal because detection signal is proportional to the number of photons of fluorescent light collected from the sample. Fluorescent light can be emitted by a sample excited by excitation light, as in fluorescence, or chemically excited, as in chemiluminescence.

The term "NA enhancing optical element" as used herein refers to a singlet or cemented assembly satisfying at least two aplanatic conditions as illustrated in FIGS. 3A–3E. The aplanatic conditions can reduce the divergence angle of a bundle of fluorescent photons emitted from any point in the sample object plane or increasing the convergence of a bundle of excitation rays delivered to any point in the object plane. The cemented surfaces can have identical curvature (infinite in the case of planar surfaces). The uncemented or outside surfaces each substantially satisfy a different aplanatic condition. A NA enhancing optical element can include a truncated sphere, a spherical surface combined with a cylindrical surface, a spherical surface combined with a planar surface, a meniscus lens, etc. The components of a NA enhancing optical element can be bonded or coupled with a fluid of suitable index that does not substantially fluoresce. The index of the fluid can be matched to material of the lens and/or the material of housing, as opposed to air. The components of a NA enhancing optical element can be stationary or movable relative to each other such as a scanning system. NA enhancing optical elements can be constructed of BK7, PBH71, LaSFN9, or other high index glasses. The term "lens" as used herein refers to a single component or singlet, such as a truncated sphere, meniscus lens, a concave lens, a convex lens, etc. or a system that can include multiple components, such as NA enhancing optical elements in FIGS. 3B, 3D, 3E, camera lenses, etc.

The term "detector" as used herein refers to any component or system of components that can detect light including a charged coupled device (CCD), back-side thinned CCD, cooled CCD, a photodiode, a photodiode array, a photomultiplier tube (PMT), a PMT array, complimentary metal-oxide semiconductor (CMOS) sensors, CMOS arrays, a charge-injection device (CID), CID arrays, etc. The term "cycle" as used herein refers to the period of time that the detector collects light before converting it to electrical signal.

The term "housing" as used herein refers to any structure that provides containment or support to the sample. The housing can be transparent to provide entry to excitation light and exit to fluorescent light. The housing can be constructed of glass, plastic such as low fluorescence plastic, fused silica such as synthetic fused silica or synthetic quartz, etc. The housing can take any shape including tubing (various types), capillaries, assemblies of capillaries, etched channel plates, molded channel plates, embossed channel plates, wells in a multi-well tray, chambers in a microcard, regions in a microslide, etc.

The term "dye" as used herein refers to any dye in any form in the sample. The dye can emit fluorescent light via fluorescence or chemiluminescence. Fluorescent dyes can be used to emit different colored light depending on the dyes used. Several dyes will be apparent to one skilled in the art of dye chemistry. One or more colors can be collected for each dye to provide identification of the dye or dyes detected. The dye can be a dye-labeled fragment of nucleotides. The dye can be a marker triggered by a fragment of nucleotides. The dye can be based or associated with other chemical species such as proteins, carbohydrates, etc.

The term "translation mechanism" as used herein refers to a mechanism for moving along at least one axis or path. The translation mechanism can move the mask, NA enhancing optical element, and/or housings. The translation mechanism can provide controllable movement mechanically (gears, pneumatic, cams, lead screws, ball screws etc.), electrically (actuators, linear motors, etc.), and/or magnetically (induced field movement, solenoids, etc.). The control can be provided by computer or electrical circuitry designed to provide the desirable movement corresponding to the detector parameters.

According to various embodiments, the sample can include a dye in a fluid or solid. The sample emits fluorescent light in all directions. The collection system collects a portion of this light, typically a cone of light. The NA of the NA enhancing optical element can determine the size of the cone of light.

According to various embodiments, as illustrated in FIG. 1, sample 10 can be bounded by housing 20. Fluorescent light 30 can be refracted to form a cone of light with a half angle 50 available for the NA enhancing optical element 40. According to Snell's Law, a change in index of refraction in the light path can refract the light and thus affect the size of the cone and therefore the quantity of light exiting the samples that can be collected by the optics. According to various embodiments, the sample 10 can have an index of refraction 1.29 to 1.41, and the housings 20 can have an index of refraction 1.46 to 1.6. According to various embodiments, an index matching fluid can be positioned between the housing 20 and the NA enhancing optical element 40. According to various embodiments, air or other fluid can be positioned between the housing 20 and the NA enhancing optical element 40.

According to various embodiments, the depth of sample along the optical axis can be small. According to various embodiments, the distance can be 30 micrometers to 200 micrometers deep. The fluorescent light can be emitted in a narrow depth of field substantially decreasing spherical aberrations. According to various embodiments, an aplanatic condition can be provided by positioning the sample at the radius of curvature of a solid lens as described in patent application U.S. Ser. No. 09/564,790 to Richard T. Reel titled "Optical System and Method for Optically Analyzing Light from a Sample" that is herein incorporated by reference in its entirety. According to various embodiments, other aplanatic conditions are described in Kidger, Michael J., *Fundamental Optical Design* (2002), herein incorporated by reference in its entirety.

Figure 2A:
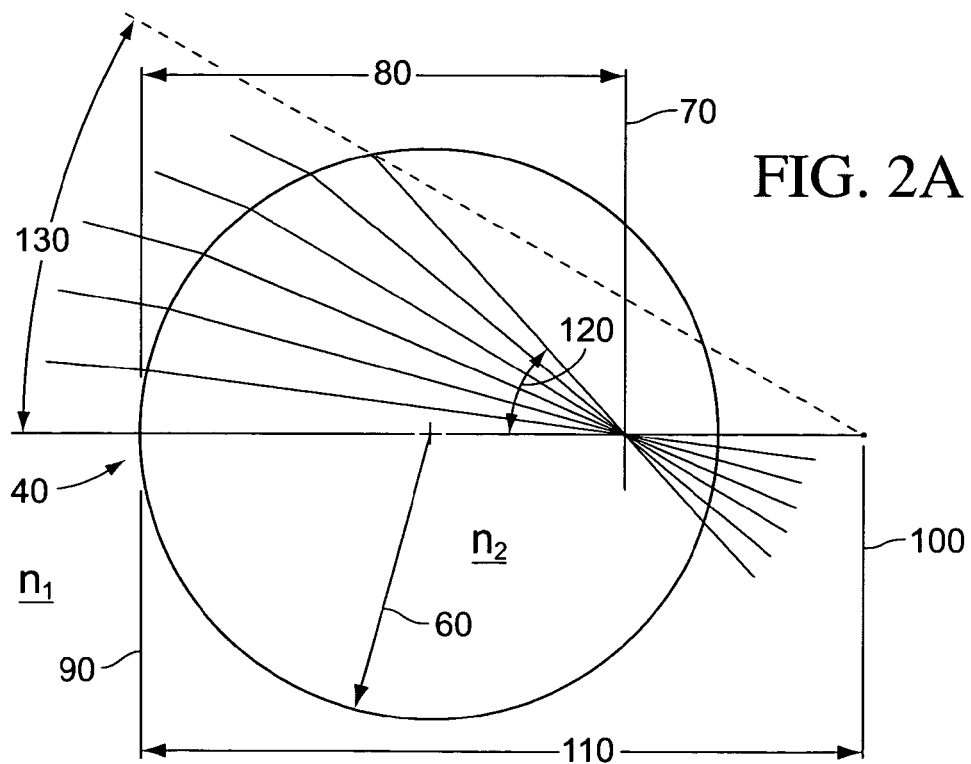
FIGS. 2A–2B illustrate cross-sectional views of various embodiments of NA enhancing optical elements.
Figure 2B:
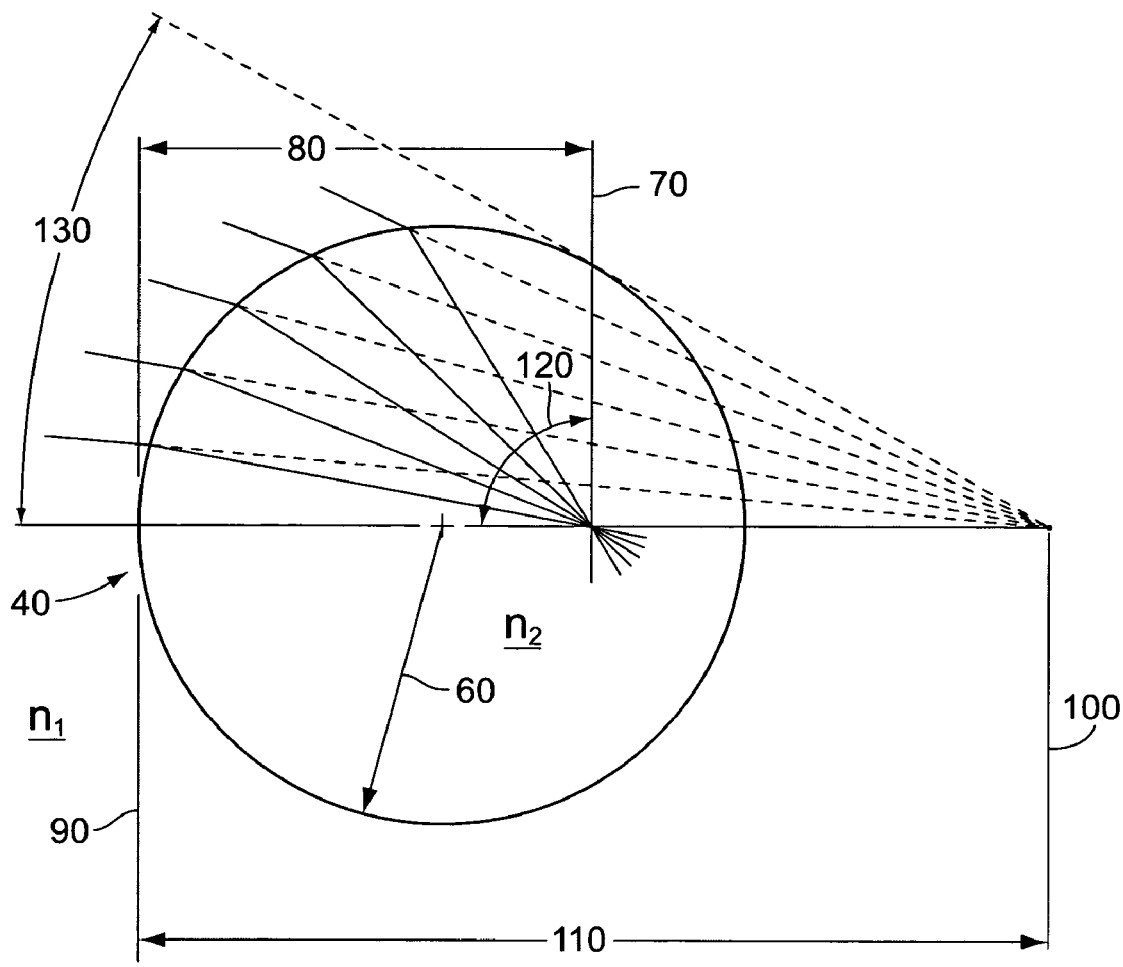

According to various embodiments, the amount of fluorescent light collected can be a function of the index of refraction ($n_2$) of the NA enhancing optical element 40 and the index of refraction ($n_1$) around the NA enhancing optical element 40. As illustrated in FIGS. 2A and 2B, NA enhancing optical element 40 can have radius (R) 60 and source plane 70 where the source plane 70 has a distance 80 from the front end 90 of NA enhancing optical element 40, where the distance 80 can be calculated as $R*(n_1+n_2)/n_2$. The NA enhancing optical element 40 can refract the fluorescent light from source plane 70 so that it appears to come from plane 100 and decrease the cone of light from half angle 120 to half angle 130 providing more collection of fluorescent light. Plane 100 has a distance 110 from the front end 90 of the NA enhancing optical element 40, where the distance 100 can be calculated as $R*(n_1+n_2)/n_1$. According to various embodiments, FIG. 2B illustrates a NA enhancing optical element 40 with a higher index of refraction than the NA enhancing optical element 40 illustrated in FIG. 2A. Examples of high index of refraction materials include fused silica (n=1.46), optical glasses such as BK7 (n=1.52) and LaSFN9 (n=1.85), and plastics such as polycarbonate (n=1.56). According to various embodiments, the material used to construct can be better served by using a low fluorescing material, low Raleigh and low Raman scattering.

Figure 3A:
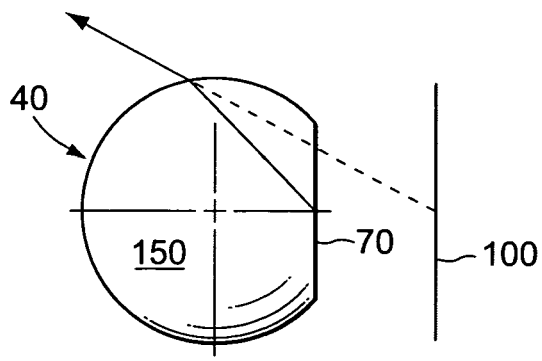
FIGS. 3A–3E and 5 illustrate cross-sectional views of various embodiments of a NA enhancing optical element.
Figure 3B:
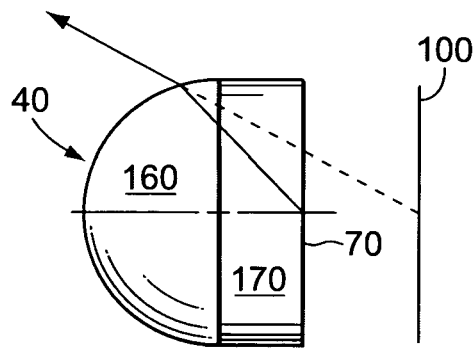
Figure 3C:
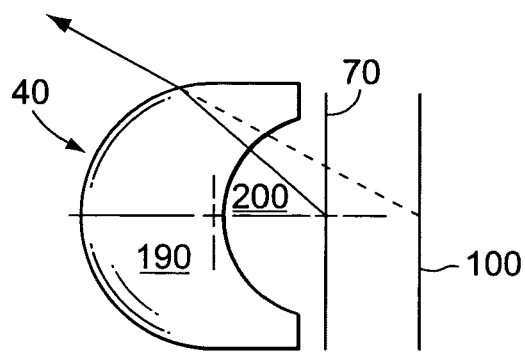
Figure 3D:
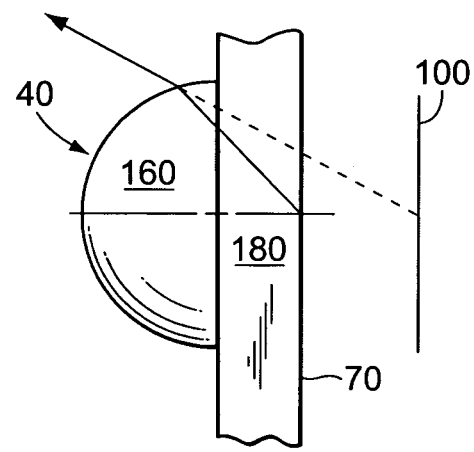
Figure 3E:
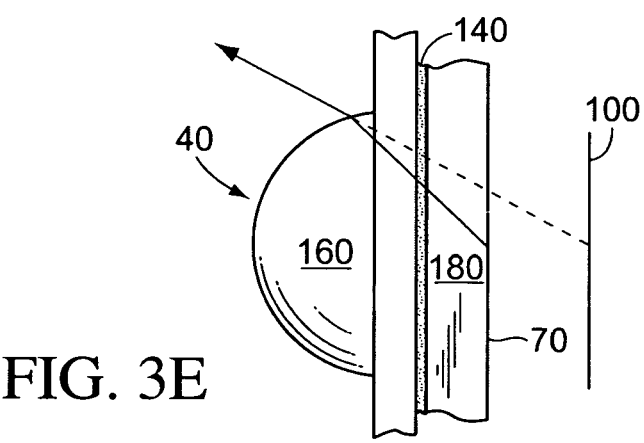

According to various embodiments, FIGS. 3A–3F illustrate different NA enhancing optical elements. FIG. 3A illustrates a NA enhancing optical element 40 including a truncated sphere 150 where the source plane 70 can be the flat portion of the truncated sphere 150. FIG. 3B illustrates a NA enhancing optical element 40 including a sphere 160 combined with a cylinder 170 where the source plane 70 can be the end of the cylinder 170. FIG. 3C illustrates a NA enhancing optical element 40 including a meniscus lens 190 where the source plane 70 can be a plane at the radius of curvature of the meniscus 200. FIG. 3D illustrates a NA enhancing optical element 40 including a sphere 160 combined with a plate 180 where the source plane 70 can be the end of the plate 180. FIG. 3E illustrates a NA enhancing optical element 40 including a sphere 160 combined with a fluid 140 and a plate 180. The sphere 160 can be bonded or coupled with the fluid 140 of similar index. The sphere 160 can be stationary or movable relative to plate 180 to provide scanning along the source plane 70.

According to various embodiments, the NA enhancing element and the housing are constructed of different material. Unlike known systems where the index of refraction of a truncated sphere and a housing are matched so that spherical aberration can be eliminated, changing the material of the NA enhancing element according to the teachings of the present invention provides a significant increase in NA enhancement with a minimal introduction of spherical aberration. Unlike known systems where an index matching fluid is added to match both truncated sphere and housings and provide a continuum minimizing the refraction of the interface of the truncated sphere and the housing, the index matching fluid matches to either the truncated sphere, the housing, or an intermediate index.

Figure 4:
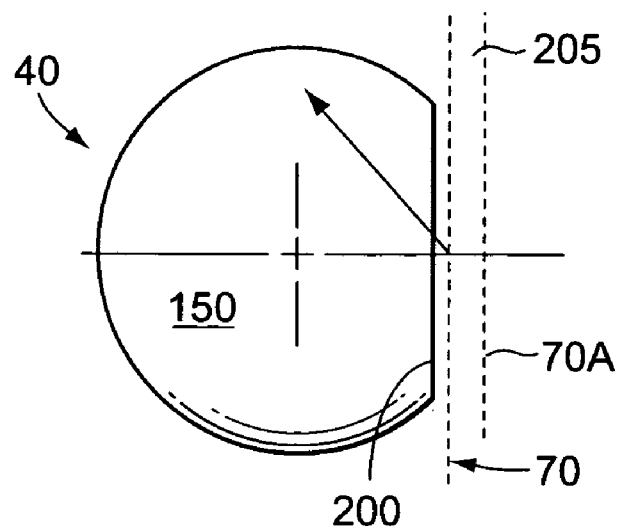
FIG. 4 illustrate the relationship of the source plane for the NA enhancing optical element and the theoretical aplanatic source plane, where
Figure 4A:
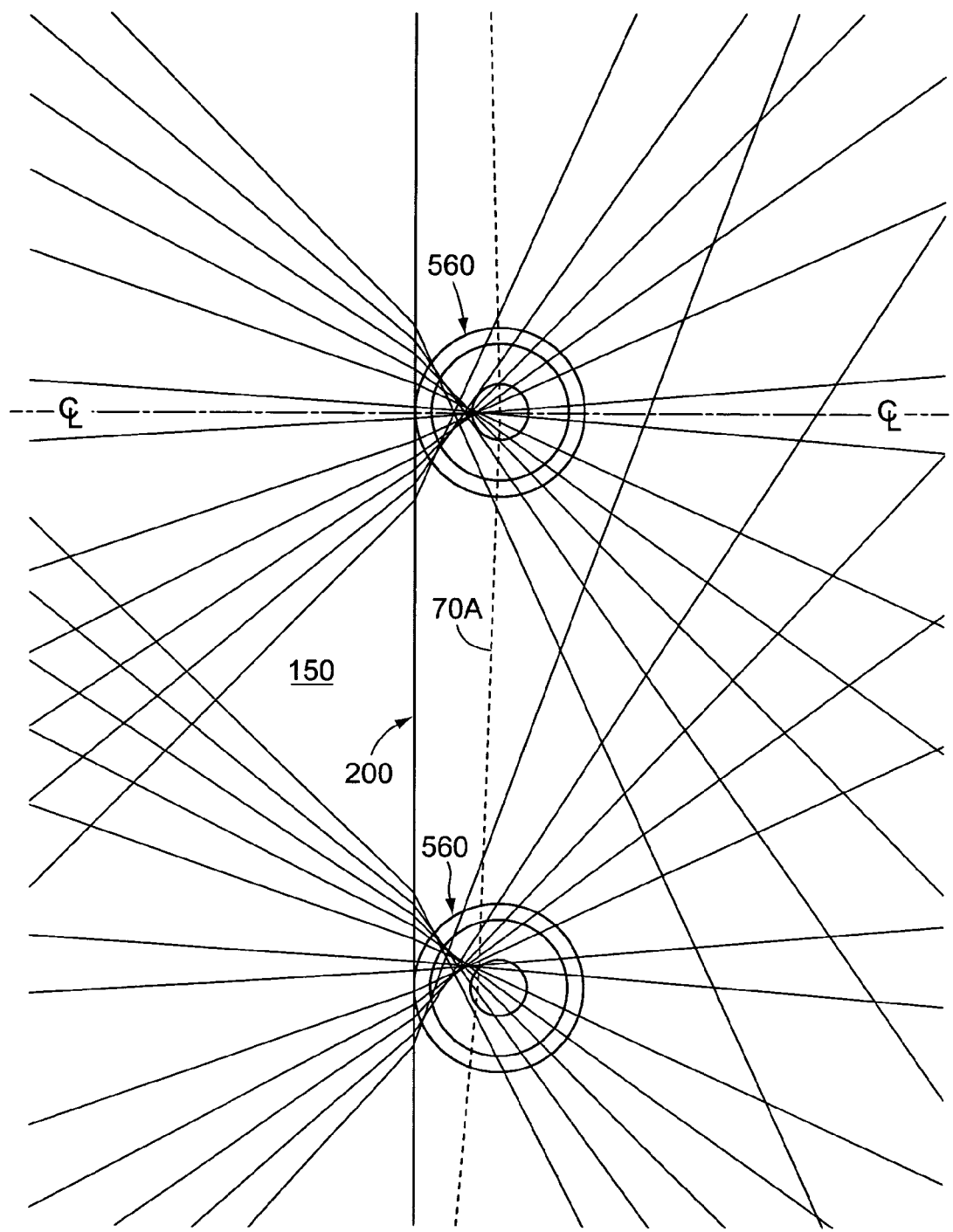
FIG. 4A illustrates the focus of light when the theoretical aplanatic source plane is used and FIG. 4B illustrates the focus of light when the source plane according to various teachings of the present invention is used.
Figure 4B:
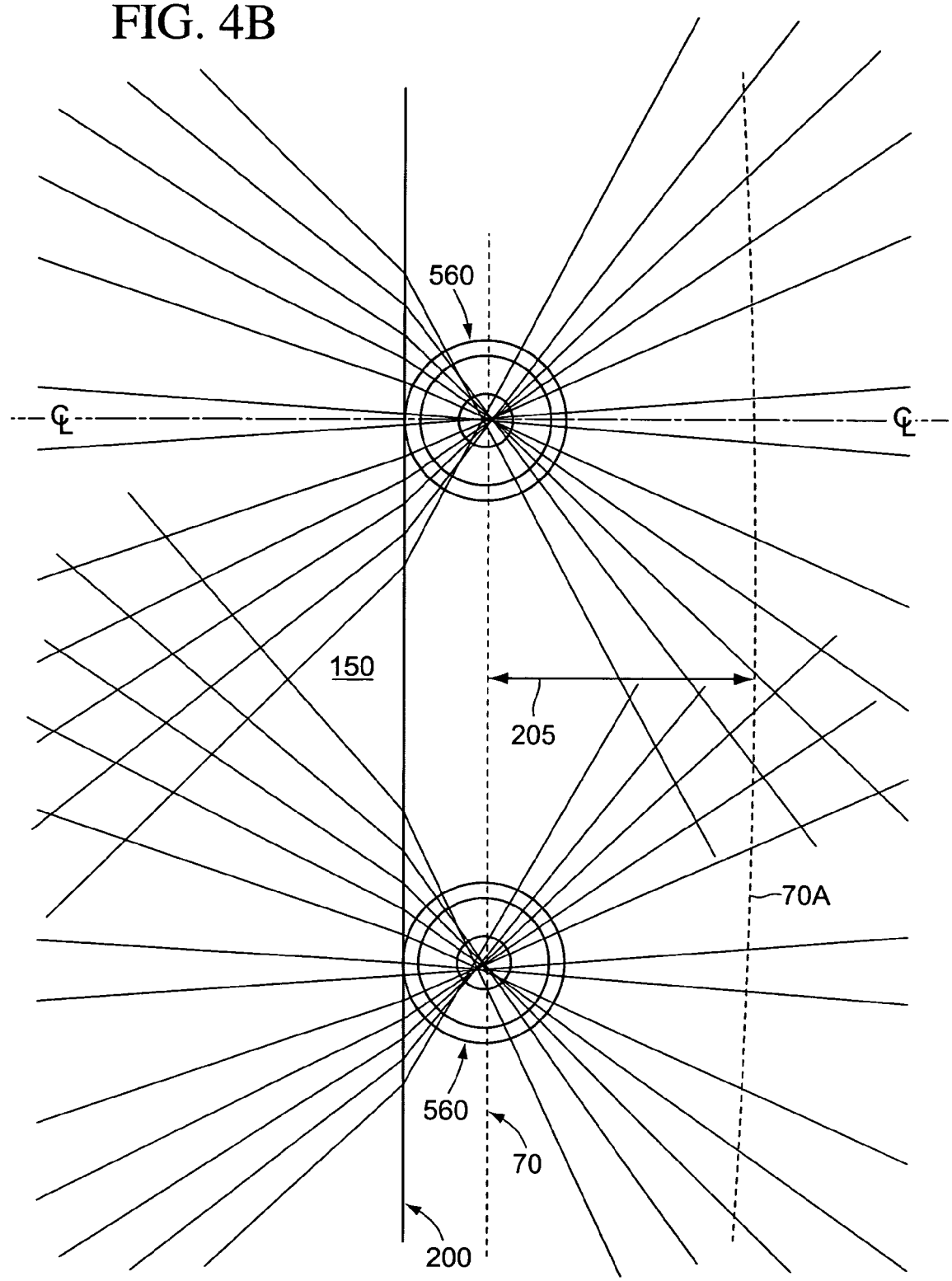

According to various embodiments, as illustrated in FIG. 4, NA enhancing optical element 40 can include truncated sphere 150 that can be truncated and/or positioned to provide an offset 205 between source plane 70 and the theoretical aplanatic source plane 70A. The offset 205 can introduce corrective aberrations to fluorescent light detection system when the truncated sphere 150 and housing 560 are constructed of different material, for example glass and fused silica. It is desirable that the index of glass be used in the truncated sphere be as high as practical. In a confocal configuration, where the NA enhancing optical element is used for excitation or collection, the improvement approximately proportional to $n^4$ each or $n^{16}$ for both excitation and collection. FIG. 4A illustrates truncating the sphere 150 and positioning the housings 560 at the theoretical aplanatic source plane 70A when the sphere 150 and the housings 560 are constructed of different material. The focus is shifted from the desirable position at the center of the housing 560. FIG. 4B illustrates truncating the sphere 150 and positioning the housings 560 at the source plane 70 that is offset 205 from the theoretical aplanatic source plane 70A. The offset 205 shift that focus to the desirable center of the housing 560 to compensate for the difference in index of refraction of the truncated sphere 150 and the housing 560.

Figure 5:
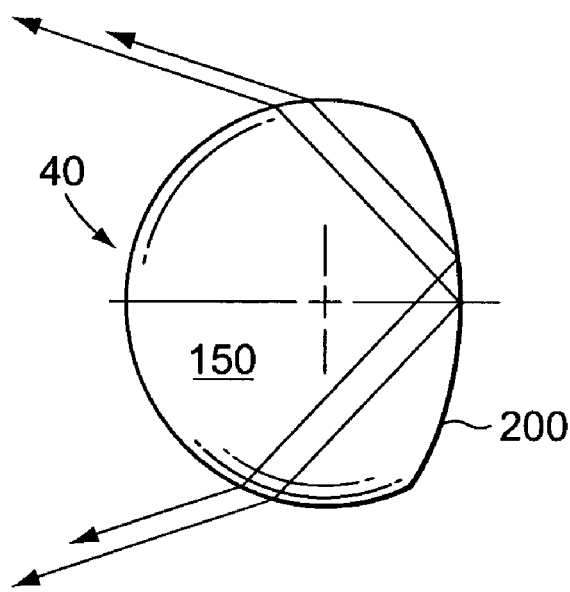

According to various embodiments, as illustrated in FIG. 5, NA enhancing optical element 40 can include truncated sphere 150 where the back end 200 is curved to provide assistance in improving imaging across a curved field of view. According to various embodiments, additional optical elements can be added to the NA enhancing optical element 40 illustrated in FIG. 5 to provide flattening of a curved field of view.

According to various embodiments, as illustrated in FIG. 6A, fluorescence light detection system 210 includes NA enhancing optical element 40 including truncated sphere 150 with offset source plane 70, lens 220, filter 240, lens 250, and detector 290. Lens 220 can form a substantially collimated region 230 with fluorescent light 30 where filter 240 can be positioned to accept desired wavelengths of the fluorescent light 30 and reject other wavelengths. Filter 240 can be an interference filter. Lens 250 can focus the fluorescent light 30 onto detector 290. According to various embodiments, FIG. 6B illustrates a fluorescent light detection system 210 similar to that illustrated in FIG. 6A except lens 260 focuses the fluorescent light 30 on filter 270 that accepts desired wavelengths of the fluorescent light 30 and rejects other wavelengths. Lens 280 focuses the fluorescent light 30 onto detector 290. Filter 270 can be positioned on a filter wheel, linear actuator, or other mechanism for switching between multiple filters.

According to various embodiments, a fluorescent light detection system can include components to spectrally separate the wavelengths of fluorescent light to provide multi-color detection including but not limited to transmission gratings, reflective gratings, prisms, grisms, software controllable filters (width and position in spectral axis) etc. According to various embodiments, the sample container or the fluorescent light detection system can be positioned to decrease motion-induced blurring on the detector. According to various embodiments, a fluorescent light detection system can include folding mirrors to decrease the size of the system.

Figure 7:
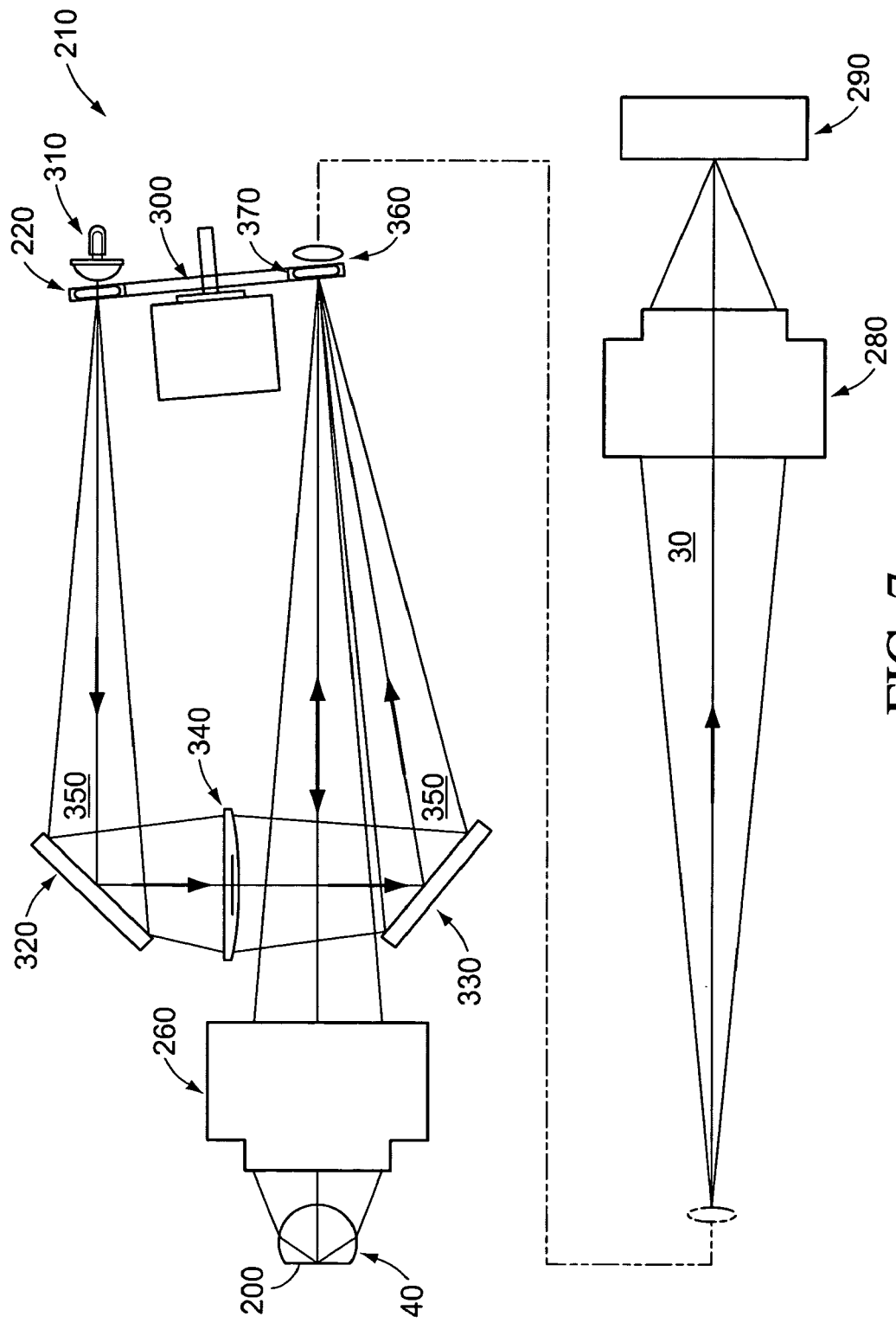

According to various embodiments, as illustrated in FIG. 7, fluorescent light detection system 210 can include light source 310, filter wheel 300 including filter 220 and filter 370, mirrors 320 and 330, lenses 340, 260, 360, and 280, NA enhancing optical element 40 including source plane 70, and detector 290. Excitation light 350 can be provided by light source 310. Excitation light can be filtered by filter 220 on filter wheel 300. Excitation light 350 can be directed to filter 370, such as a dichroic filter, on filter wheel 300 by mirrors 320 and 330 and lens 340. The filter 370 reflects excitation light 350 towards lens 260, NA enhancing optical element 40, and a sample at source plane 70. The large collection angle of NA enhancing optical element 40 can provide an increased amount of light from light source 310 to a small detection spot of the sample. The excitation light 350 can be absorbed by the sample or dyes in the sample that can emit fluorescent light 30. Fluorescent light 30 can be collected by NA enhancing optical element 40 and directed to lens 260 and filter 370. The color of fluorescent light 30 can pass through filter 370 to lens 360 and lens 280 that focus the fluorescent light 30 onto detector 290. The image can be magnified to reduce the collection angle to one that is suitable for the detector 290. According to various embodiments, lens 500 can be larger in diameter than lens 430 to avoid vignetting by making the angle of incidence for the reflection of the dichroic mirror 480 be less than 45 degrees to improve transmission and reflection properties.

Figure 8:
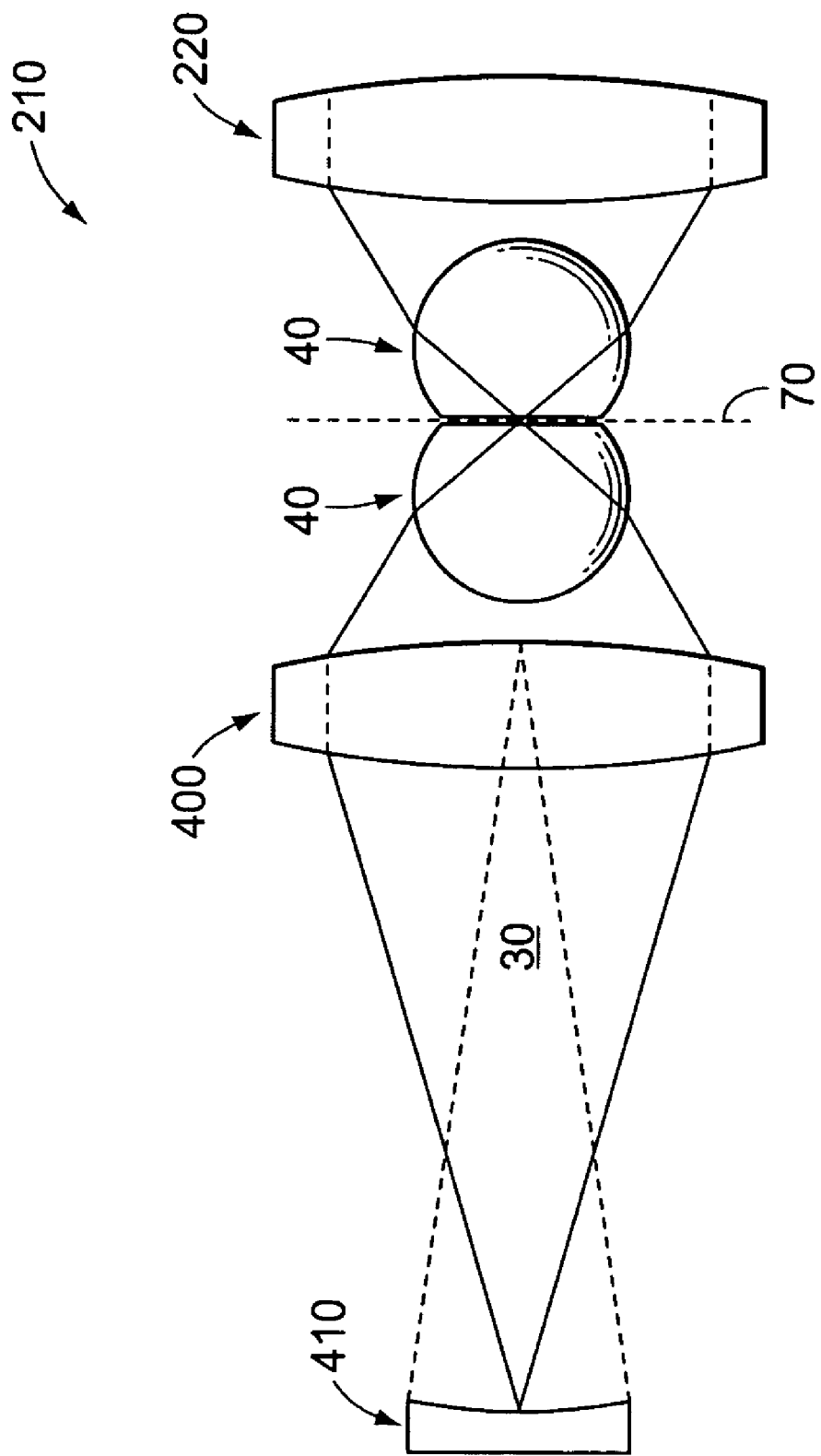
Figure 9:
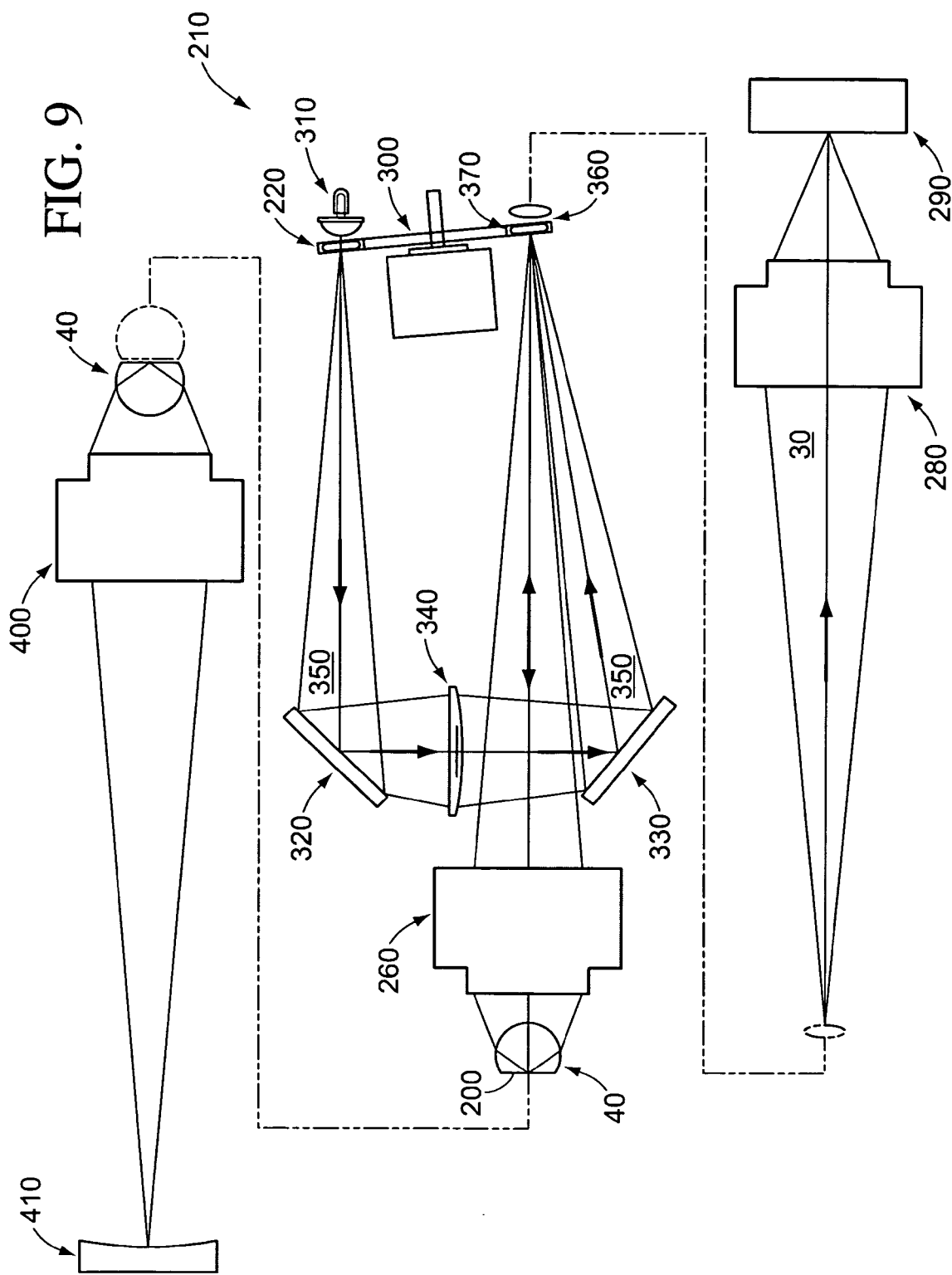

According to various embodiments, as illustrated in FIG. 8, fluorescent light detection system 210 can include two NA enhancing optical elements 40 to collect fluorescent light from both sides of the sample. The fluorescent light 30 on the opposite side of detector 290 can be collected and directed back towards detector 290 through lens 400 and mirror 410, such as a concave mirror. The fluorescent light 30 reflected from mirror 410 can be directed back through both NA enhancing optical elements 40 (co-imaged across source plane 70), lenses 220 and 250, and filter 240 toward detector 290. Collecting light from both sides of the sample can double the amount of excitation light as well as doubling the amount of fluorescent light 30 directed toward the detector 290 resulting in a 4× improvement. According to various embodiments, FIG. 9 illustrates a fluorescent light detection system 210 similar to the one illustrated in FIG. 7 with two NA enhancing optical elements 40 and a mirror 410 as illustrated in FIG. 8.

According to various embodiments, a fluorescent light detection system can include a mask providing an aperture to reduce cross-talk between multiple samples. According to various embodiments, the mask can be positioned to provide excitation and collection of fluorescent light from a single sample. According to various embodiments, samples can be positioned so that the mask provides excitation light to and collection of fluorescent light from a single sample. According to various embodiments, the mask can be positioned to provide excitation and collection of fluorescent light from a subset of samples. According to various embodiments, samples can be positioned so that the mask provides excitation and collection of fluorescent light from a subset of samples. According to various embodiments, a fluorescent light detection system can be positioned to collect fluorescent light from each sample on different portions of the detector thereby collecting individually while detecting collectively.

Figure 10:
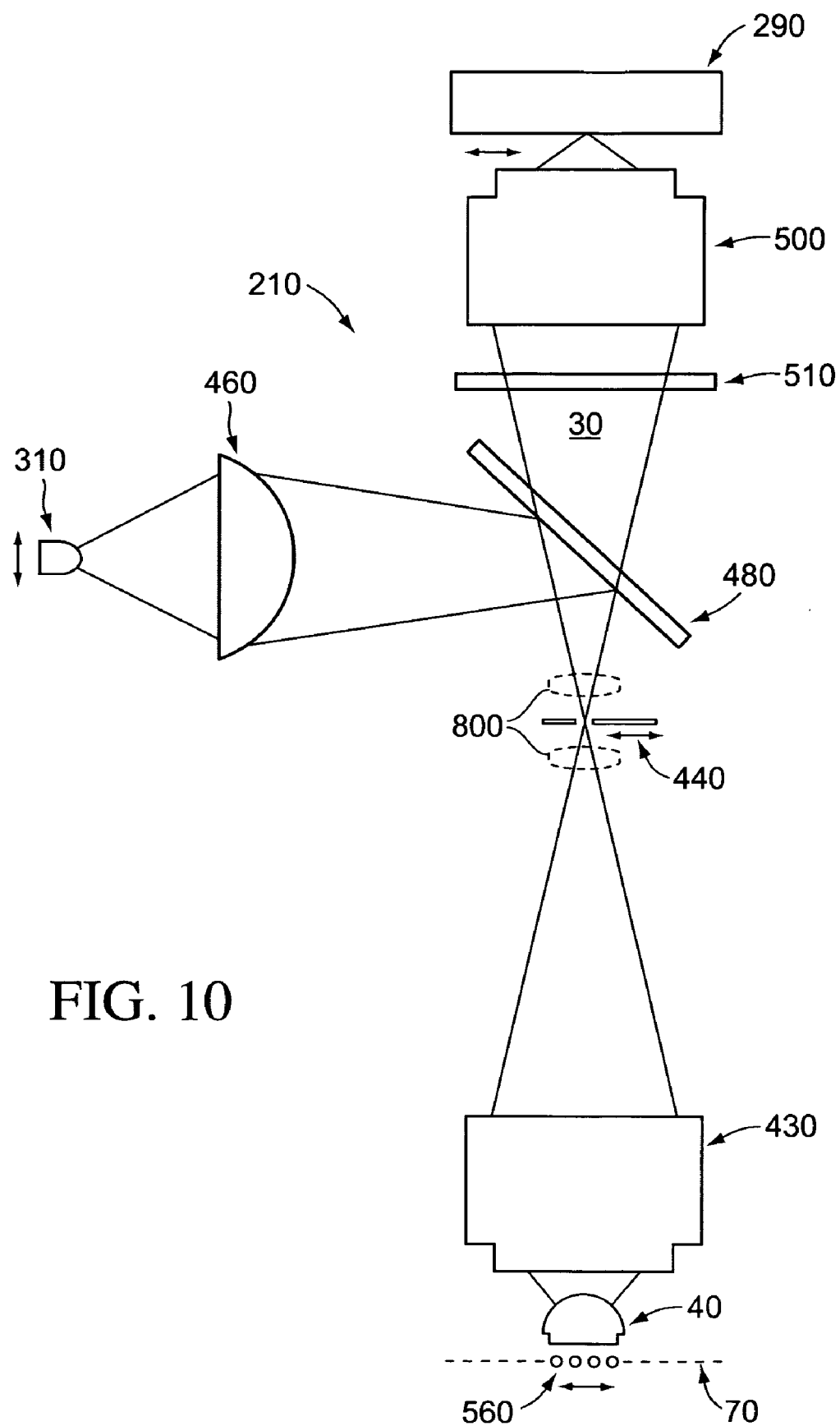

According to various embodiments, as illustrated in FIG. 10, fluorescent light detection system 210 can include sample housings 560, NA enhancing optical element 40, lenses 430, 460, 520, 500 and 800, dichroic beam-splitter 480, light source 310, mask 440, grating 510 and detector 290. According to various embodiments, mask 440 can be positioned to reduce cross-talk between multiple samples, as illustrated by the double arrow near the mask. Lenses 800, which can be positioned on either side of the mask as indicated by the broken lines, can focus light on mask 440 while remaining stationary. According to various embodiments, light source 310 can be positioned in coordination with positioning mask 440, as illustrated by the double arrow near the light source. The light source can be narrow on the order of only one aperture in the mask. Hence, the light source can be positioned from aperture to aperture in a mask by scanning with more than one aperture. According to various embodiments, sample housings 560 and/or NA enhancing optical element 40 can be positioned to reduce cross-talk between multiple samples, as illustrated by the double arrow near the sample housings. According to various embodiments, lens 500 and/or detector 290 can be positioned to reduce cross-talk between multiple samples, as illustrated by the double arrow between the lens and detector. According to various embodiments, a mirror can be positioned to direct where the image falls on the detector. According to various embodiments, the detector can be masked to control where the image falls on the detector.

Figure 11A:
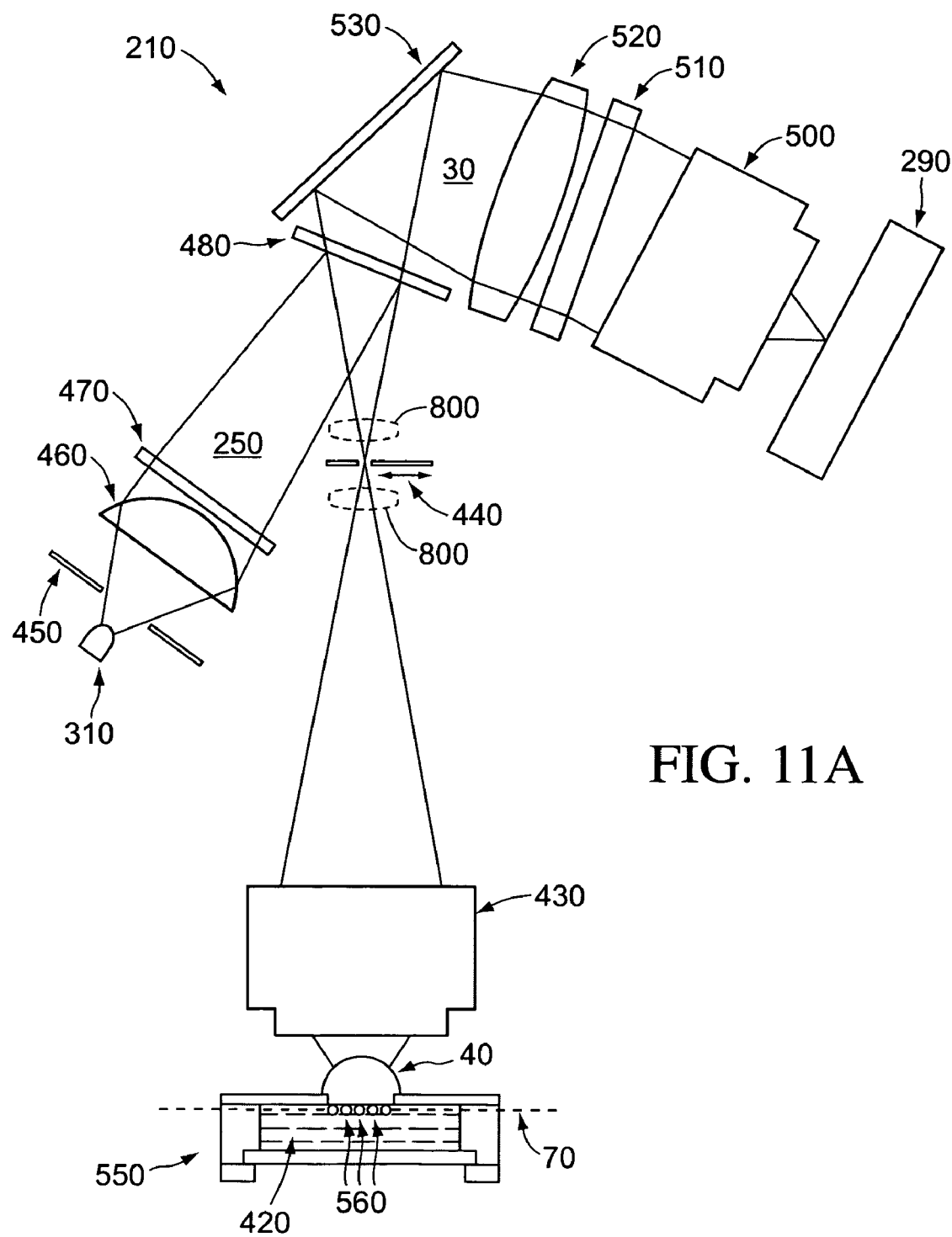
FIG. 11A illustrates a diagrammatical view of various embodiments of a light detection system.

According to various embodiments, as illustrated in FIG. 11A, fluorescent light detection system 210 can include assembly 550 that can include sample housings 560 in index matching fluid 420, NA enhancing optical element 40, lenses 430, 500, 520, 460, and 800, dichroic beam-splitter 480, filter 470, mirror 530, grating 510 and mask 440. The light source 310 can provide excitation light 250 to lens 460 that can collect the excitation light 250 from the source. Excitation light 250 can be directed to filter 470 that can condition the excitation light 250 by accepting desirable wavelengths of excitation light 250 while blocking other wavelengths. For example, filter 470 can be a bandpass filter that accepts wavelengths that excite a dye in the sample and block wavelengths that correspond to the wavelengths of the fluorescent light emitted by the dyes. Excitation light 250 can be reflected by dichroic mirror 480 to pass through an aperture in mask 440. Mask 440 can be positioned at an image plane of lens 430. The mask 440 can translate along the image plane as illustrated by the double arrow. Lenses 800 can focus light on mask 440 while remaining stationary. Excitation light 250 can be directed to NA enhancing optical element 40 and focused onto housings 560 that can be positioned in source plane 70. Excitation light 250 can be absorbed by dyes in the samples in housings 560, stimulating the dyes to emit fluorescent light 30 in all directions. NA enhancing optical element 40 can collect fluorescent light 30 and direct it to lens 430 and mask 440. The aperture in mask 440 can bound excitation light 250 and fluorescent light 30 to one housing 560 thereby reducing cross-talk between fluorescent light emitted from other housings 560. Fluorescent light 30 can pass through dichroic mirror 480, while non-fluorescent light can be rejected. Fluorescent light 30 can be reflected by mirror 530, substantially collimated by lens 520, dispersed by transmission grating 510, and focused by lens 500 onto detector 290.

Figure 11B:
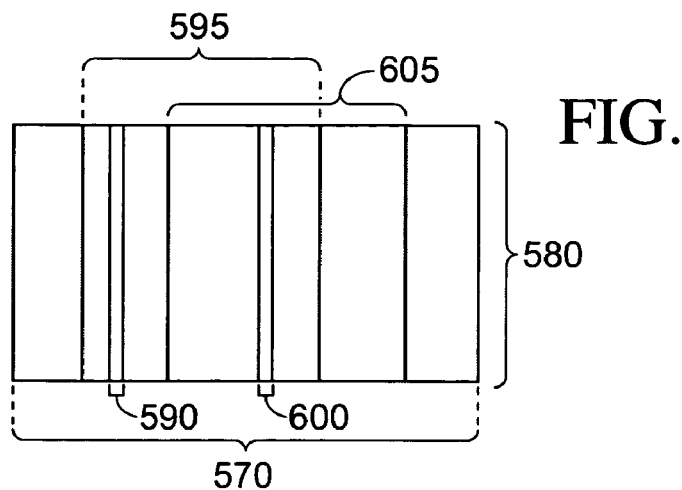
FIG. 11B illustrates a diagrammatical view of various embodiments of a portion of a detector as illustrated in FIG. 11A.

According to various embodiments, FIG. 11B illustrates a magnified view of portion 540 of detector 290 illustrated in FIG. 11A. Portion 540 has a spectral axis 570 and a spatial axis 580. Fluorescent light 30 from a single housing 560 can be dispersed across band 595 of the detector. Regions of the detector, for example 590 and 600 collect different wavelengths of light and can be measured to determine the spectral composition of the fluorescent light. Light from other housings 560 dispersed across band 605 can be displaced on the detector so different regions can be selected. The overlap of bands 595 and 605 can be reduced by clearing the detector after light from each housing is read. According to various embodiments, the region 590 can be 520 nanometers and region 600 can be 700 nanometers. According to various embodiments, fluorescent light can be collected from the detection zone while bands of dye move through the housing. According to various embodiments, blurring induced by the motion of bands of dye can be reduced by shifting the packets of charges on the detector at the same velocity as the image of the moving bands of dye on the detector. The velocity of the bands of dye passing the detection zone can be predicted because the bands of dye move at a predictable rate through the housing. The velocity of the bands of dye in the detection zone can be calculated by dividing the known separation distance by the measured separation time. According to various embodiments, the packets of charges on the detector can be accumulated by time-delay integration as described in U.S. Ser. No. 10/205, 028 to Nordman et al. titled "Time-Delay Integration in Electrophoretic Detection Systems" that is herein incorporated by reference in its entirety. According to various embodiments, the mask can be positioned to excite and/or detect a different housing and/or subset of housings. According to various embodiments, the fluorescent light detection system can cycle through all the housings and/or subsets of housings such that the bands of dye detected at the beginning of the cycle have traveled no more than the full length of the detection zone during a cycle. Each cycle can capture a portion of the electropherogram from each housing. The spatial axis of the image of fluorescent bands can be converted from distance to time to create a conventional electropherogram. According to various embodiments, the number of housings that can fit on the source plane for the collector lens can determine the desirable cycling times/rate.

Figure 12A:
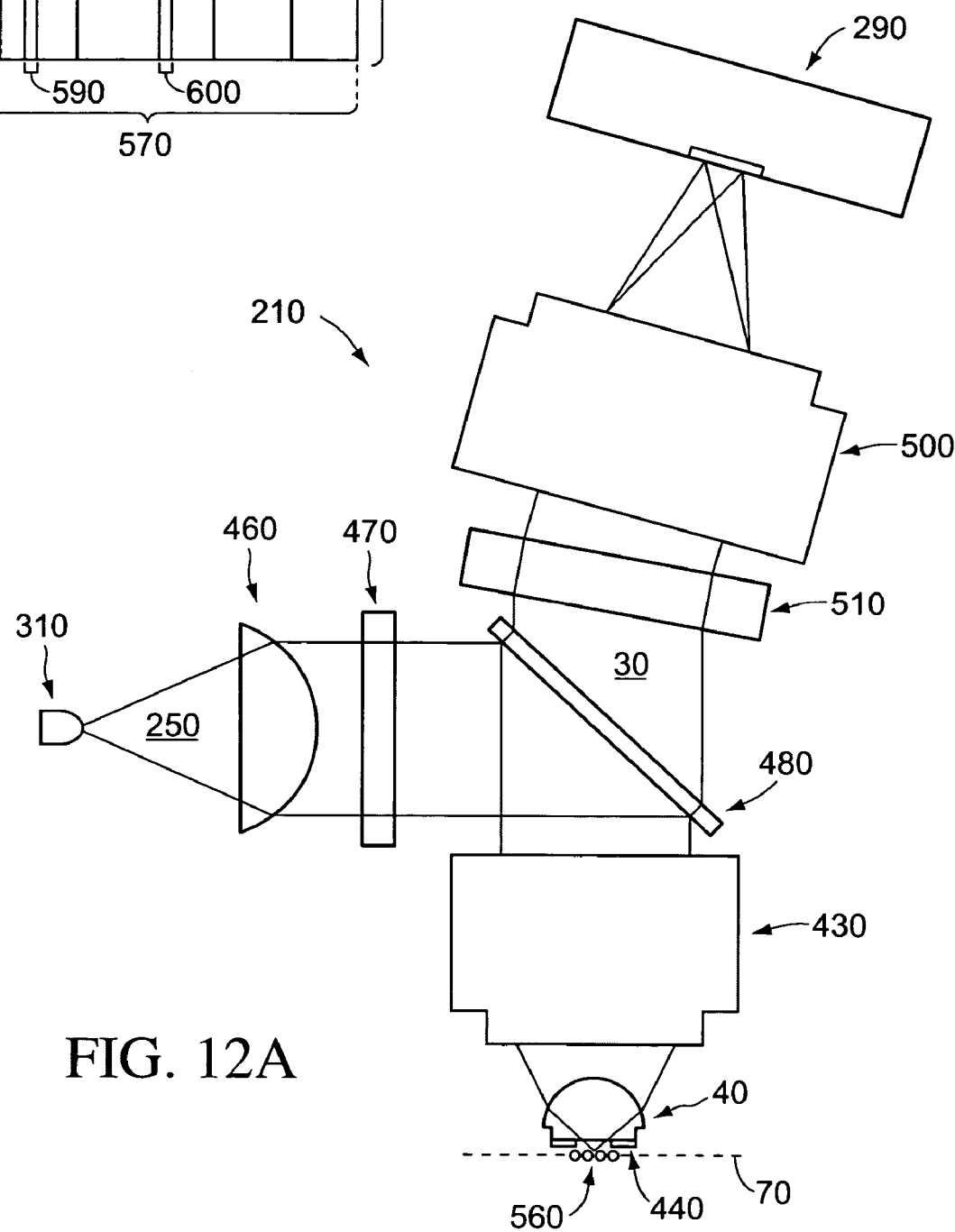
FIG. 12A illustrates a diagrammatical view of various embodiments of a light detection system.

According to various embodiments, as illustrated in FIG. 12A, fluorescent light detection system 210 can include light source 310, lenses 460, 430, and 500, NA enhancing optical element 40, filter 470, grating 510, dichroic mirror 480, detector 290, housings 560, and mask 440. The light source 310 can provide excitation light 250 to lens 460 that can collect the excitation light 250 from the source. Excitation light 250 can be directed to filter 470 that can condition the excitation light 250 by accepting desirable wavelengths of excitation light 250 while blocking other wavelengths. For example, filter 470 can be a bandpass filter that accepts wavelengths that excite a dye in the sample and block wavelengths that correspond to the wavelengths of the fluorescent light emitted by the dyes. Excitation light 250 can be reflected by dichroic mirror 480 and directed to NA enhancing optical element 40 by lens 430 to be focused onto housings 560 through mask 440, where the housings 560 can be positioned in source plane 70 offset from NA enhancing optical element 40. Excitation light 250 can be absorbed by dyes in the samples in housings 560, stimulating the dyes to emit fluorescent light 30 in all directions.

Figure 12B:
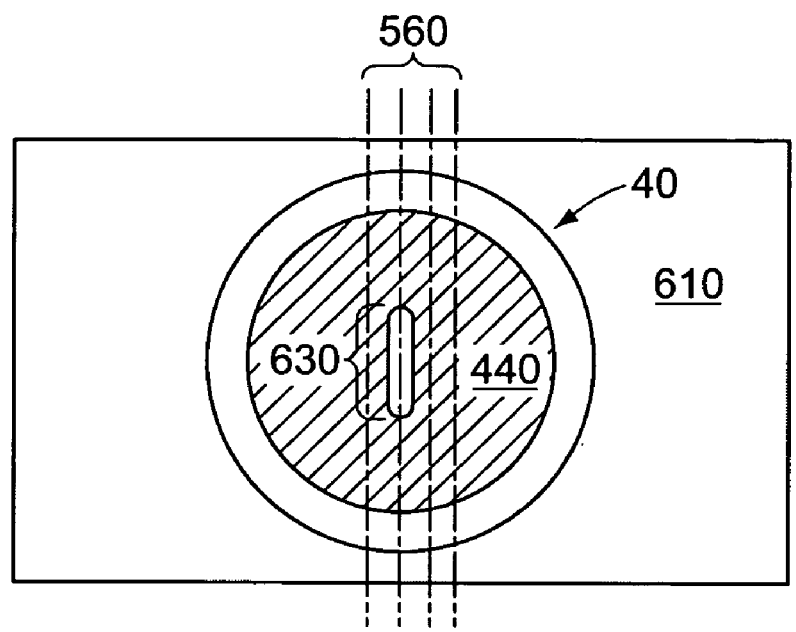
FIG. 12B illustrates a cross-sectional top view of a portion of various embodiments of a light detection system as illustrated in FIG. 12A.
Figure 12C:
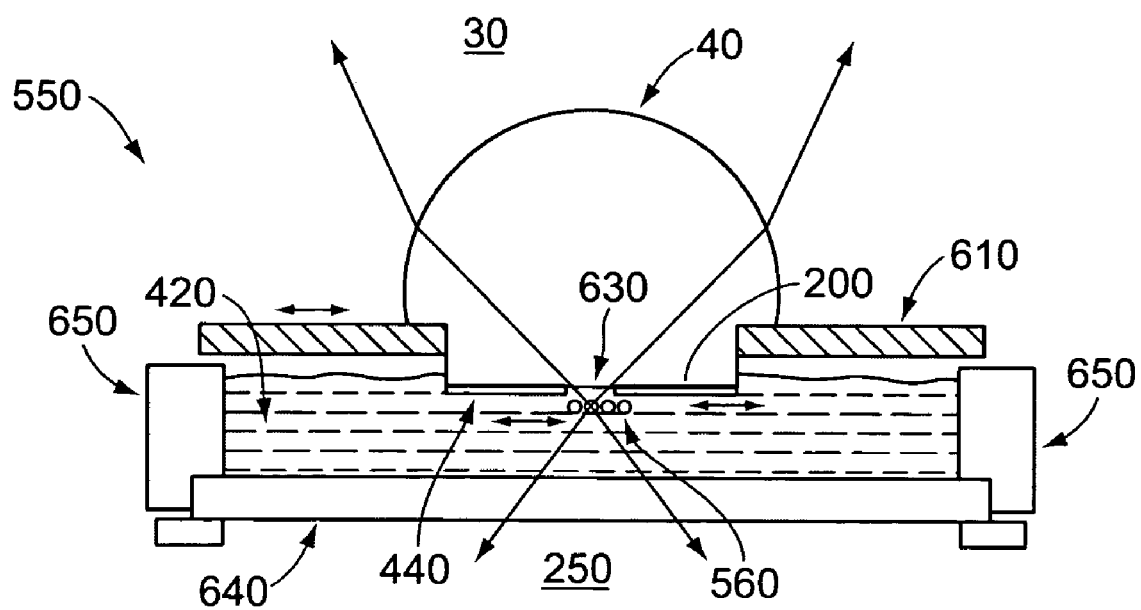
FIG. 12C illustrates a cross-sectional side view of a portion of various embodiments of a light detection system as illustrated in FIG. 12A.

According to various embodiments, the fluorescent light detection system illustrated in FIG. 12A can include a mechanism to translate housings 560 in the source plane 70 so that mask 440 can align with one housing or a subset of the housings. This translation is illustrated in FIG. 12C as a double-headed arrow near housing 560. According to various embodiments, as illustrated in FIG. 12B, mask 440 can be coupled to the back end 200 of NA enhancing optical element 40 so that the aperture in mask 440 provides detection zone 630. NA enhancing optical element 40 can collect fluorescent light 30 from the detection zone 630 and direct it to lens 430. The detection zone 630 in mask 440 can bound excitation light 250 and fluorescent light 30 to one housing or subset of housings thereby reducing cross-talk between fluorescent light emitted from other housings 560. Fluorescent light 30 can pass through dichroic mirror 480, while non-fluorescent light can be rejected. Fluorescent light 30 can be dispersed by transmission grating 510, and focused by lens 500 onto detector 290.

According to various embodiments, as illustrated in FIG. 12C, the housings 560 can be positioned in assembly 550 so that the housings 560 are immersed in index matching fluid 420. Assembly 550 can include NA enhancing, optical element holder 610 and base 650. Mask 440 can be coupled to back end 200 of NA enhancing optical element 40 so that the aperture in mask 440 provides detection zone 630. Mask 440 can be a coating applied to the back end 200 of NA enhancing optical element 40. According to various embodiments, the base 650 can be translated to position housings 560 and index matching fluid 420 so that mask 440 can provide detection zone 630 to the desired position to collect fluorescent light from one housing or a subset of housings. According to various embodiments, the housings 560 can be positioned in sequence to align with the detection zone 630. According to various embodiments, base 650 can include baffling 640. Baffling 640 can form the bottom of assembly 550. According to various embodiments, baffling 640 can include an anti-reflective window to permit the excitation light 250 and/or fluorescent light 30 to exit assembly 550 on the opposite side of NA enhancing optical element 40. For example, the window can be constructed of fused silica coated with an AR material to minimize background light. According to various embodiments, baffling 640 can include a mirror to reflect fluorescent light 30 and increase the amount of fluorescent light 30 transmitted through NA enhancing optical element 40. According to various embodiments, the mirror can be a spherical surface as illustrated in FIGS. 8 and 9.

Figure 12D:
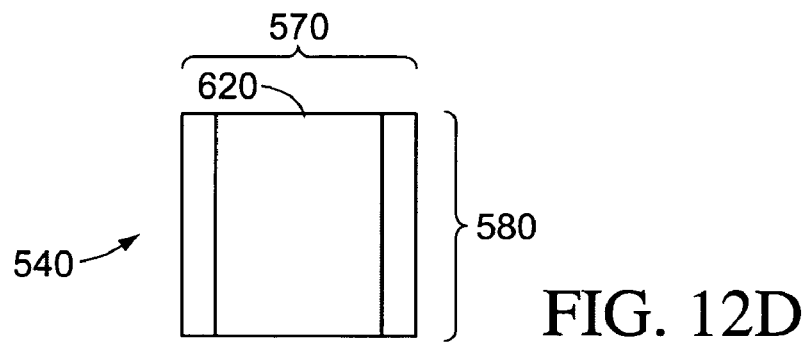
FIGS. 12D–E illustrate diagrammatical views of various embodiments of a portion of a detector as illustrated in FIG. 12A.

According to various embodiments, FIG. 12D illustrates a magnified view of portion 540 of detector 290 illustrated in FIG. 12A. Portion 540 has a spectral axis 570 and a spatial axis 580. Fluorescent light 30 from a single housing 560 can be spectrally separated into different wavelengths, for example band 620. According to various embodiments, overlapping bands can be prevented by collecting fluorescent light 30 from each housing 560 before switching to next housing 560. The integration time to collect light from each housing 560 can limit the number of housings 560. According to various embodiments, band 620 can range from 520 nanometers and 700 nanometers. According to various embodiments, the number of housings that can be positioned by the base can be determined by at least one of the base translation time, detector collection time, size of detection zone, and sample rate. According to various embodiments, sample rate can include rate at which sample travels through housing and/or rate of electrophoresis.

Figure 12E:
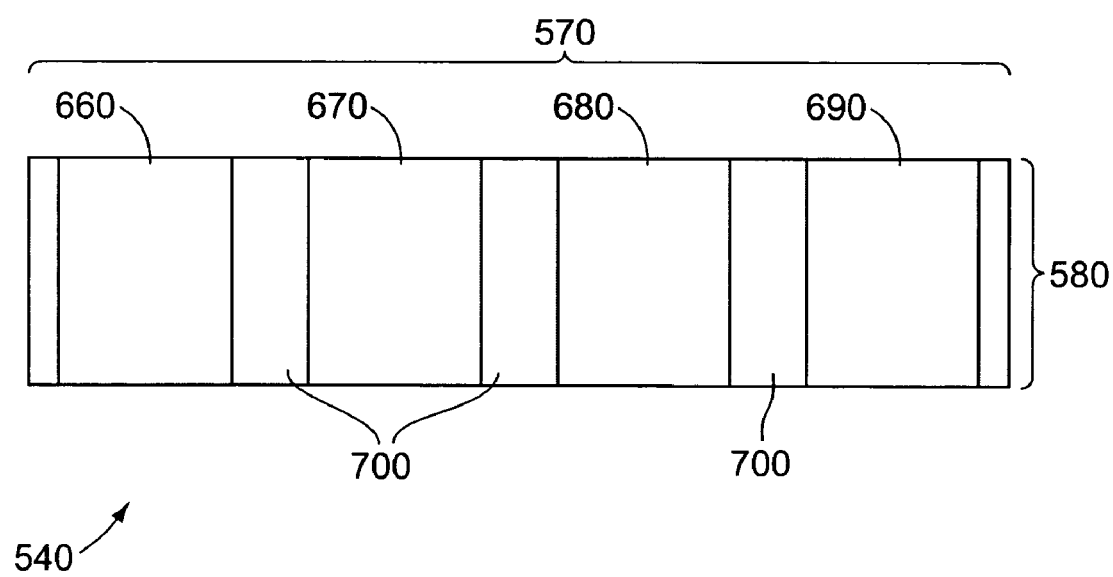

According to various embodiments, the fluorescent light detection system illustrated in FIG. 12A can include a translation mechanism to move NA enhancing optical element 40. This translation is illustrated by the double-headed arrow near holder 610. According to various embodiments, as illustrated in FIGS. 12B and 12C and described herein, NA enhancing optical element 40, mask 440, and assembly 550 can be similar to a system that includes a translation mechanism to move the housings 560. Detection zone 630 can be positioned by the translation mechanism to move the NA enhancing optical element 40. According to various embodiments, FIG. 12E illustrates a magnified view of portion 540 of detector 290 illustrated in FIG. 12A. Portion 540 has a spectral axis 570 and a spatial axis 580. Fluorescent light 30 can be detected at different wavelengths from each housing 560, for example bands 660, 670, 680, and 690, each from a different housing 560. According to various embodiments, each band 660, 670, 680, and 690 can range from 520 nanometers and 700 nanometers. According to various embodiments, the pitch or spacing of the housings 560 can be provided such that bands of adjacent housings 560 do not overlap, as illustrated in FIG. 12E. The wavelength bands for each housing 560 can be detected on the detector 290 at one interval without having to be detected separately. According to various embodiments, the detector can accumulate packets of charges by time-delay integration. The detector collection time can be matched to the sample rate.

According to various embodiments, gaps 700 can provide a range of wavelengths to permit bandpass filter 470 to exclude sufficient wavelengths to reduce overlap between bands 660, 670, 680, and 690 on portion 540 of detector 290. According to various embodiments, pitch, P, can be calculated: P=S*R/M, wherein S is the number of pixels on detector 290 to capture one of bands and a gap, R is the width per pixel, and M is the magnification. According to various embodiments, the size of the detector 290 can determine the number of housings 560 detected at the same time.

Figure 13:
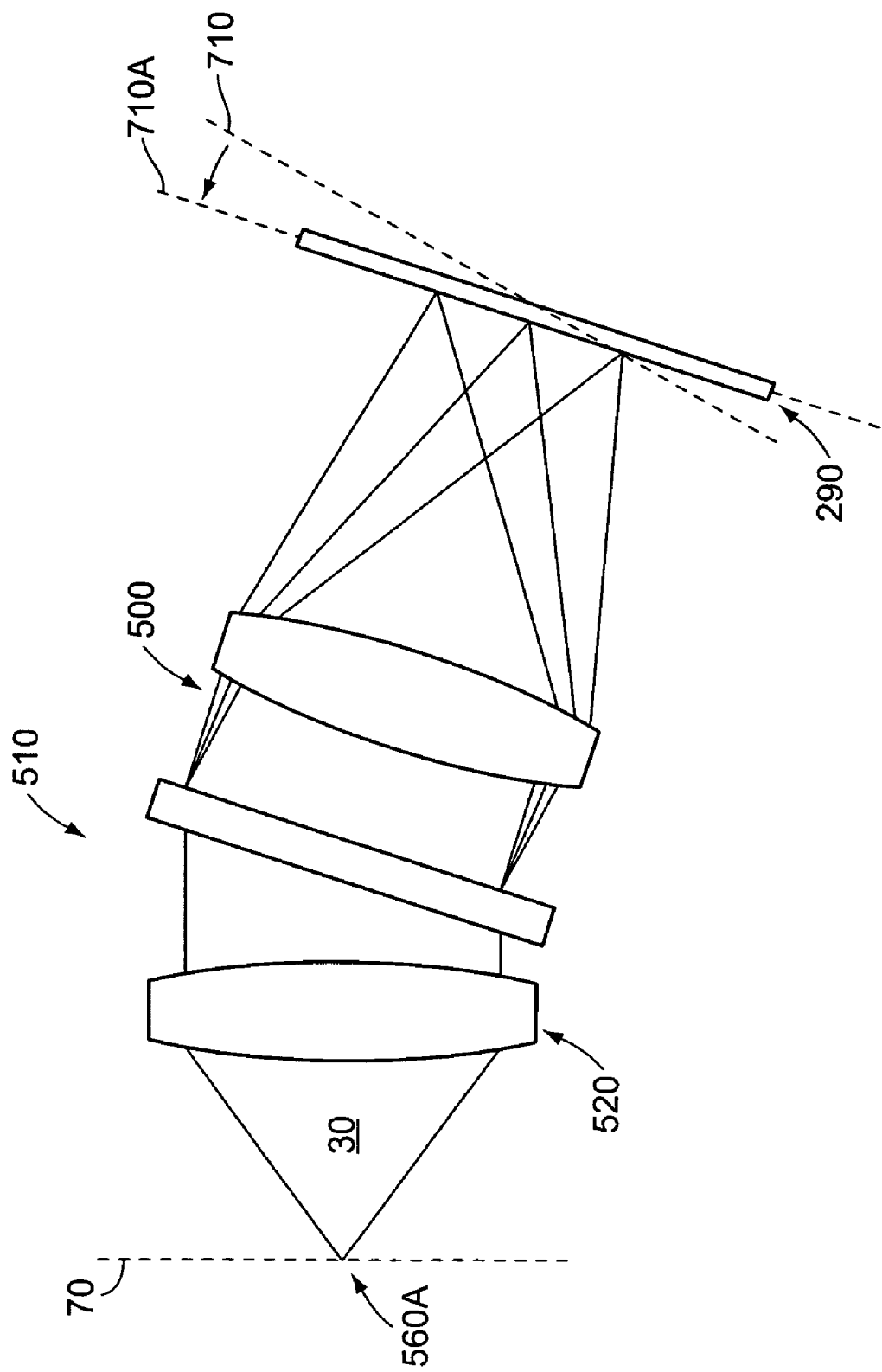
FIG. 13 illustrates a diagrammatical view of various embodiments of a light detection system.

According to various embodiments, as illustrate in FIG. 13, chromatic aberrations can be reduced by tilting the detector 290 and positioning housings 560 such that source plane 70 tilts. For example, tilting source plane 70 to position 70A as illustrated by the arrow and tilting the plane 710 of detector 290 to position 710A provides detection of fluorescent light 30 collected from housing 560A to be detected by wavelength band 720A and fluorescent light 30 collected from housing 560B to be detected by wavelength band 720B. According to various embodiments, a fluorescent light detection system including the tilting illustrated in FIG. 13, can reduce chromatic aberrations by distancing different colors.

According to various embodiments, the fluorescent light detection system illustrated in FIG. 12A can include a mechanism to translate mask 440. This translation is illustrated by the double-headed arrow near mask 440 in FIG. 12C. According to various embodiments, as illustrated in FIGS. 12B and 12C and described herein, NA enhancing optical element 40, mask 440, and assembly 550 can be similar to system that includes a translation mechanism to move the housings 560 except that the mask 440 is not coupled to NA enhancing optical element 40. Detection zone 630 can be positioned by the mechanism to translate the mask 440. According to various embodiments, as illustrated in FIG. 12D and described herein, the fluorescent light detection system can provide band 620 to a portion 540 of detector 290.

Figure 14:
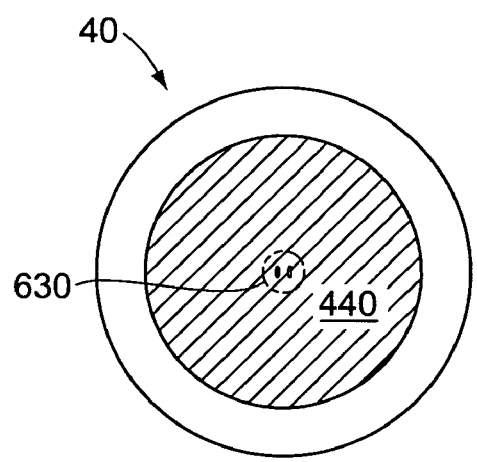
FIGS. 14–14A illustrate cross-sectional top views of various embodiments of a NA enhancing optical element and mask.
Figure 14A:
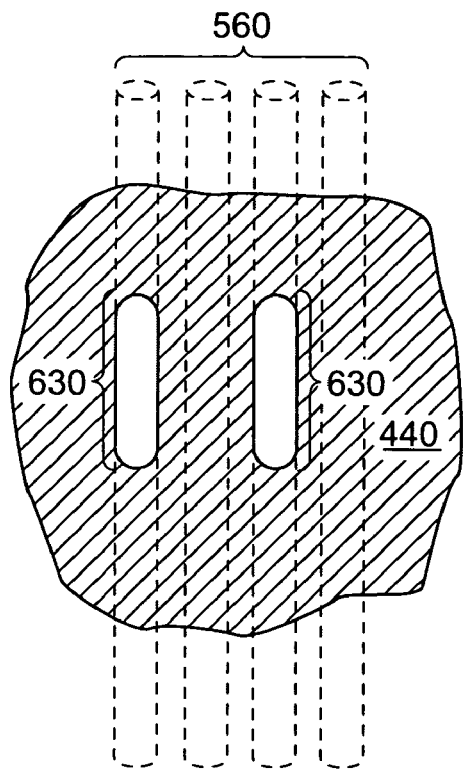
Figure 14B:
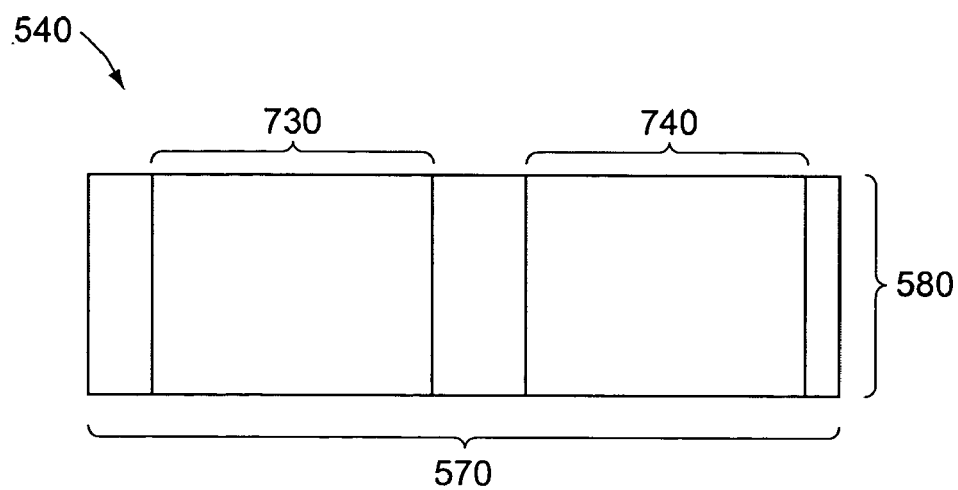

According to various embodiments, the fluorescent light detection system can collect fluorescent light from a subset of housings. According to various embodiments, the mask can include two or more apertures to provide multiple detection zones. According to various embodiments, the apertures can be aligned such that fluorescent light can be collected from non-adjacent housings. This can provide collection of fluorescent light from multiple housings. According to various embodiments, as illustrated in FIGS. 14 and 14A, mask 440 can include multiple detection zones 630. According to various embodiments, as illustrated in FIG. 14B, portion 540 of detector 290 can detect fluorescent light collected from a first detection zone as wavelength band 730 and from a second detection zone as wavelength band 740 without overlap. According to various embodiments, the fluorescent light detection system can include a dichroic mirror that provides bandpass filtering to reject wavelengths outside the range of interest to reduce overlap of wavelength bands.

Figure 15:
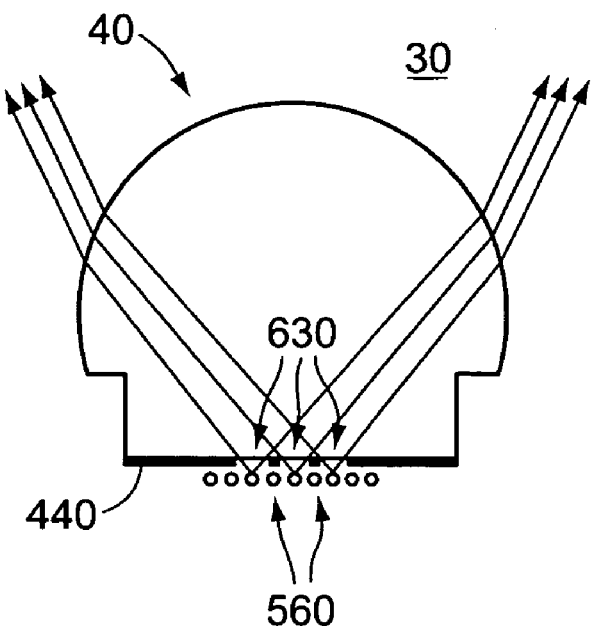
FIGS. 15–16 illustrate cross-sectional side views of various embodiments of NA enhancing optical element, mask, and housing configurations.
Figure 16:
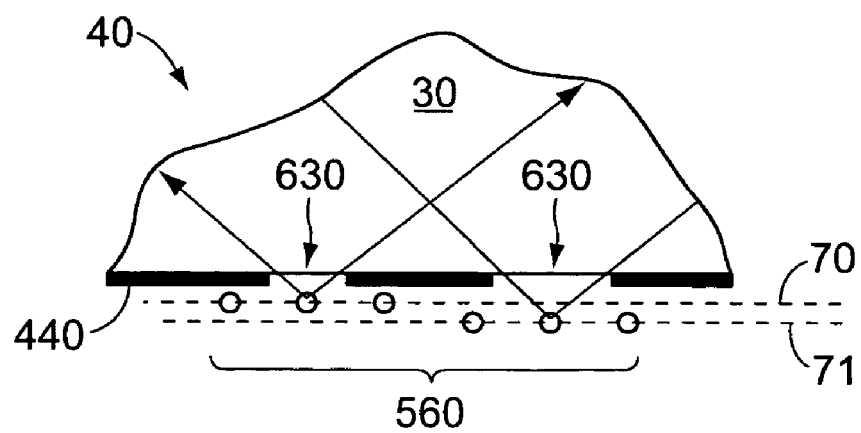

According to various embodiments, as illustrated in FIG. 15, mask 440 can include multiple apertures to provide detection zones 630 to collect fluorescent light 30 from non-adjacent housings 560. According to various embodiments, as illustrated in FIG. 16, mask 440 can include two apertures to provide detection zones 630 to collect fluorescent light 30 from non-adjacent housings 560. Housings 560 can be tilted from source plane 70 to source plane 71 to compensate for tilting detector 290 to reduce chromatic aberrations. According to various embodiments, the fluorescent light can be collected from the remaining housings by at least one of: (1) translating the housings 560; (2) translating the NA enhancing optical element 40 coupled to the mask 440; (3) translating the mask not coupled to the NA enhancing optical element 40 wherein the mask can be positioned between the housings 560 and NA enhancing optical element 40; and (4) translating the mask not coupled to the NA enhancing optical element 40 wherein the mask can be positioned between NA enhancing optical element 40 and detector 290.

According to various embodiments, the fluorescent light detection system can be included in an instrument for detection of fluorescent light from electrophoresis. According to various embodiments, the fluorescent light detection system can be included in an instrument for detection of fluorescent light from flow cytometry. According to various embodiments, the fluorescent light detection system can be included in an instrument for detection of fluorescent light from liquid chromatography, such as high-pressure liquid chromatography (HPLC).

According to various embodiments, a method for fluorescent light detection can include providing a plurality of housings for the samples, providing a NA enhancing optical element, providing a mask, and positioning the mask to reduce cross-talk between fluorescent light from the samples. According to various embodiments, positioning the mask can include positioning the mask between the NA enhancing optical element and the plurality of housings. According to various embodiments, positioning the mask further include translating the plurality of housings. According to various embodiments, positioning the mask can include translating the NA enhancing optical element and the mask. According to various embodiments, positioning the mask can include translating the mask. According to various embodiments, positioning the mask can include positioning the mask between the NA enhancing optical element and a detector.

All publications and patent applications referred to herein are hereby incorporated by reference to the same extent as if each individual publication or patent application was specifically and individually indicated to be incorporated by reference.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a mask" includes two or more different masks. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A fluorescent light detection system for analyzing biological samples comprising:
    at least one NA enhancing optical element; and
    at least one housing for the samples,
    wherein the NA enhancing optical element is constructed of a first material and the housing is constructed of a second material, wherein the first material has a greater index of refraction than the second material, and
    wherein the samples being detected are located in a source plane offset from the theoretical aplanatic source plane of the NA enhancing optical element.

2. The system of claim 1, wherein the offset is configured to provide corrective aberration.

3. The system of claim 1, wherein the NA enhancing optical element is a truncated sphere.

4. The system of claim 3, wherein the truncated sphere is truncated such that the source plane substantially intersects the center of the housings.

5. A fluorescent light detection system for analyzing biological samples comprising:
    a NA enhancing optical element;
    a plurality of housings for the samples;
    a mask comprising at least one aperture adapted to reduce cross-talk of fluorescent light from the samples; and
    a translation mechanism, wherein the translation mechanism is adapted to move at least one of the NA enhancing optical element, the plurality of housings, and the mask.

6. The system of claim 5, wherein the NA enhancing optical element is a truncated sphere.

7. The system of claim 6, wherein the mask is positioned between a back end of the truncated sphere and the plurality of housings.

8. The system of claim 7, wherein the mask is coupled to the back end of the truncated sphere.

9. The system of claim 6, wherein the mask is positioned between a front end of the truncated sphere and the detector.

10. The system of claim 6, further comprising a detector adapted to detect fluorescent light from multiple housings per cycle.

11. The system of claim 6, wherein the detector provides time-delay integration.

12. The system of claim 6, wherein the detector is tilted to reduce chromatic aberration.

13. The system of claim 6, further comprising a detector adapted to detect fluorescent light from one housing per cycle.

14. The system of claim 6, wherein the translation mechanism provides translation of a detection zone, wherein the translation substantially matches the speed of the samples in the housings.

15. The system of claim 6, wherein the mask comprises multiple apertures adapted to correspond to non-adjacent housings.

16. The system of claim 6, further comprising a grating adapted to provide fluorescent light from multiple dyes to a detector.

17. A fluorescent light detection method for analyzing biological samples comprising:
    enhancing the NA of the system with a NA enhancing optical element; and
    reducing cross-talk between fluorescent light from samples in a plurality of housings.

18. The method of claim 17, wherein enhancing NA comprises truncating a spherical lens, and coupling the truncated sphere to at least one housing, wherein the spherical lens is constructed of a first material and the housing is constructed of a second material, such that the first material has a greater index of refraction than the second material.

19. The method of claim 18, wherein reducing cross-talk comprises positioning a mask between the truncated sphere and the plurality of housings.

20. The method of claim 19, wherein positioning the mask further comprises translating the plurality of housings.

21. The method of claim 19, wherein positioning the mask further comprises translating the truncated sphere and the mask.

22. The method of claim 19, wherein positioning the mask further comprises translating the mask.

23. The method of claim 18, reducing cross-talk comprises positioning a mask between the truncated sphere and a detector.

24. The method of claim 23, wherein positioning the mask further comprises translating the mask.

25. A fluorescent light detection system for analyzing samples comprising:
    means for enhancing NA;
    means for housing the samples; and
    means for reducing cross-talk of fluorescent light from samples in multiple means for housing.

26. A fluorescent light detection system for analyzing samples comprising:
    means for enhancing NA;
    means for housing the samples;
    means for reducing cross-talk of fluorescent light from samples in multiple means for housing; and
    means for correcting aberration.

* * * * *